(12) United States Patent
Slone

(10) Patent No.: US 12,222,342 B1
(45) Date of Patent: Feb. 11, 2025

(54) SYSTEMS AND METHODS FOR DETERMINING FLUID QUALITY

(71) Applicant: Simple Labs, Inc., Calistoga, CA (US)

(72) Inventor: Mike Slone, Calistoga, CA (US)

(73) Assignee: SIMPLE LABS, INC., Calistoga, CA (US)

( * ) Notice: Subject to any disclaimer, the term of this patent is extended or adjusted under 35 U.S.C. 154(b) by 0 days.

(21) Appl. No.: 18/810,608

(22) Filed: Aug. 21, 2024

(51) Int. Cl.
*G01N 33/18* (2006.01)
*G01N 31/22* (2006.01)

(52) U.S. Cl.
CPC ........ *G01N 33/18* (2013.01); *G01N 31/221* (2013.01); *G01N 31/222* (2013.01)

(58) Field of Classification Search
CPC .. G01N 21/8507; G01N 15/075; G01N 27/07; G01N 21/359; G01N 21/534; G01N 2021/7763; G01N 21/255; G01N 21/65; G01N 27/4165; G01N 2021/7759; G01N 2021/6421; G01N 21/63; G01N 27/00; G01N 15/0227; G01N 15/0205; G01N 2201/06113; G01N 33/18; G01N 31/221; G01N 31/222
See application file for complete search history.

(56) References Cited

U.S. PATENT DOCUMENTS

| | | | |
|---|---|---|---|
| 4,138,638 A * | 2/1979 | Amano | G01N 27/38 324/425 |
| 6,363,784 B1 * | 4/2002 | Gregory | G01F 23/2925 73/293 |
| 2016/0061640 A1 * | 3/2016 | Joshi | G01F 15/18 73/197 |

* cited by examiner

*Primary Examiner* — Tarun Sinha
(74) *Attorney, Agent, or Firm* — Evergreen Valley Law Group; Kanika Radhakrishnan

(57) ABSTRACT

The present invention relates to systems and methods for determining fluid quality. The system includes a sensing device. The sensing device includes an outer housing and an inner housing inserted within the outer housing. The sensing device includes a plurality of sensors configured to detect one or more parameters related to a fluid stored in a receptacle and ambient parameters of the receptacle. The sensing device further includes a control circuitry configured to generate sensory data based on the parameters related to the fluid and the ambient parameters of the receptacle. Further, the system includes a central control module. The central control module predicts, by one or more Artificial Intelligence (AI) models, the fluid quality of the fluid stored in the receptacle based on the sensory data. The AI models predict the fluid quality of the fluid based on mapping the sensory data with the set of predefined fluid quality profiles.

20 Claims, 13 Drawing Sheets

SYSTEMS AND METHODS FOR DETERMINING FLUID QUALITY

TECHNICAL FIELD

The present invention relates to electronic systems for monitoring fluid quality, and more particularly relates to systems and methods for determining quality of fluid (e.g., wine, bourbon, etc.) stored in containers.

BACKGROUND

Containers storing liquids may be configured to store for prolonged period of time ranging from several months to years. For example, alcoholic beverages such as wine, beer, rum, whisky, and the like may require storage in a barrel (or a container) for an extended period of time during their production. However, some containers may not be fully airtight, whether by design or due to limitations, leading to potential loss of liquid through evaporation, leakage, or other means, which can reduce the volume over time. For example, wooden barrels containing the liquids may evaporate naturally over the time, which is a necessary part of the distillation process. Further, the airtight seal may be crucial for spirits like whiskey and bourbon, but in case of wine, airtight seal may serve to monitor the health of the liquid inside the barrel. Numerous processes are monitored by manually sampling the containers and such existing processes are costly and labor intensive. Further, infrequent testing increases the risk of adverse reactions in the containers. Furthermore, the cost and effort associated with manual testing prevent the users (e.g., winemakers) from determining concentrations of key components in real time.

In recent times, Internet-based computing networks used in combination with wireless sensors allow users to access real-time data on wireless devices. Typically, wireless sensors are used in many industries to provide convenient and useful ways of obtaining data. One such example is sensor devices used for monitoring and determining the quality of alcohol stored in the container. However, there are several potential problems and challenges associated with the existing technologies. For example, the sensors used may experience drift over time which further leads to inaccurate readings unless regularly calibrated. Further, the sensors may have limitations in their accuracy and precision, leading to errors in the recorded data. Some of the existing sensors may not be sensitive enough to detect subtle changes in conditions or quality. However, the existing technologies may provide sensor performance of single days or hours, resembling dots on a map rather than showing trends over time. Additionally, environmental factors such as extreme temperature changes and high humidity or condensation may affect the sensor performance and accuracy, resulting in false readings and cause malfunctions.

Therefore, there is a need for systems and methods for determining quality of fluid stored in containers that overcome the aforementioned deficiencies along with providing other advantages.

SUMMARY

Various embodiments of the present disclosure disclose systems and methods for determining quality of fluid (e.g., wine, bourbon, etc.) stored in containers.

In an embodiment, a sensing device is disclosed. The sensing device includes an outer housing. The outer housing includes a cavity extending from a bottom portion to a central portion of the outer housing along a longitudinal axis of the outer housing. The cavity is adapted to receive a portion of a fluid stored in a receptacle while the sensing device is inserted into the receptacle. Further, the sensing device includes an inner housing. The inner housing includes a top part and a bottom part. The bottom part is configured in conformity with the cavity of the outer housing, for enabling the bottom part to snuggly fit onto the cavity of the outer housing while the inner housing is inserted within the outer housing through a top portion of the outer housing. The sensing device includes a plurality of sensors configured to detect at least one or more parameters related to the fluid stored in the receptacle and ambient parameters of the receptacle. The sensing device further includes a control circuitry communicably coupled to the plurality of sensors. The control circuitry is configured to at least generate sensory data based at least on processing the one or more parameters related to the fluid stored in the receptacle and the ambient parameters of the receptacle. The sensory data is transmitted to a central control module for determining quality of the fluid stored in the receptacle.

In another embodiment, a system for determining fluid quality is disclosed. The system includes a sensing device. The sensing device includes an outer housing. The outer housing includes a cavity extending from a bottom portion to a central portion of the outer housing along a longitudinal axis of the outer housing. The cavity is adapted to receive a portion of a fluid stored in a receptacle while the sensing device is inserted into the receptacle. Further, the sensing device includes an inner housing. The inner housing includes a top part and a bottom part. The bottom part is configured in conformity with the cavity of the outer housing, for enabling the bottom part to snuggly fit onto the cavity of the outer housing while the inner housing is inserted within the outer housing through a top portion of the outer housing. The sensing device includes a plurality of sensors configured to detect at least one or more parameters related to the fluid stored in the receptacle and ambient parameters of the receptacle. The sensing device further includes a control circuitry communicably coupled to the plurality of sensors. The control circuitry is configured to at least generate sensory data based at least on processing the one or more parameters related to the fluid stored in the receptacle and the ambient parameters of the receptacle. Further, the system includes a central control module communicably coupled to the control circuitry. The central control module includes a memory storing machine-executable instructions, and a processor communicably coupled to the memory. The processor is configured to execute the machine-executable instructions to cause the central control module to at least receive the sensory data from the control circuitry via a communication interface associated with the sensing device. The central control module is caused to predict, by one or more Artificial Intelligence (AI) models associated with the central control module, the fluid quality of the fluid stored in the receptacle based, at least in part, on the sensory data. The fluid quality is determined by the one or more AI models by mapping the sensory data with a data model comprising a set of predefined fluid quality profiles.

In another embodiment, a method for determining fluid quality is disclosed. The method includes detecting, by a plurality of sensors of a sensing device, at least one or more parameters related to fluid stored in a receptacle and ambient parameters of the receptacle. The method further includes generating, by a control circuitry of the sensing device, sensory data based at least on processing the one or more parameters related to the fluid stored in the receptacle and the ambient parameters of the receptacle. Further, the method includes receiving, by a central control module, the sensory data from the control circuitry via a communication interface associated with the sensing device. The method includes predicting, by one or more Artificial Intelligence (AI) models associated with the central control module, the fluid quality of the fluid stored in the receptacle based, at least in part, on the sensory data. The fluid quality is determined by the one or more AI models by mapping the sensory data with a data model including a set of predefined fluid quality profiles.

BRIEF DESCRIPTION OF THE FIGURES

The following detailed description of illustrative embodiments is better understood when read in conjunction with the appended drawings. For the purposes of illustrating the present disclosure, exemplary constructions of the disclosure are shown in the drawings. However, the present disclosure is not limited to a specific device, or a tool and instrumentalities disclosed herein. Moreover, those in the art will understand that the drawings are not to scale. Wherever possible, like elements have been indicated by identical numbers.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features.

Various embodiments of the present invention are described hereinafter with reference to FIG. 1 to FIG. 9.

Figure 1:
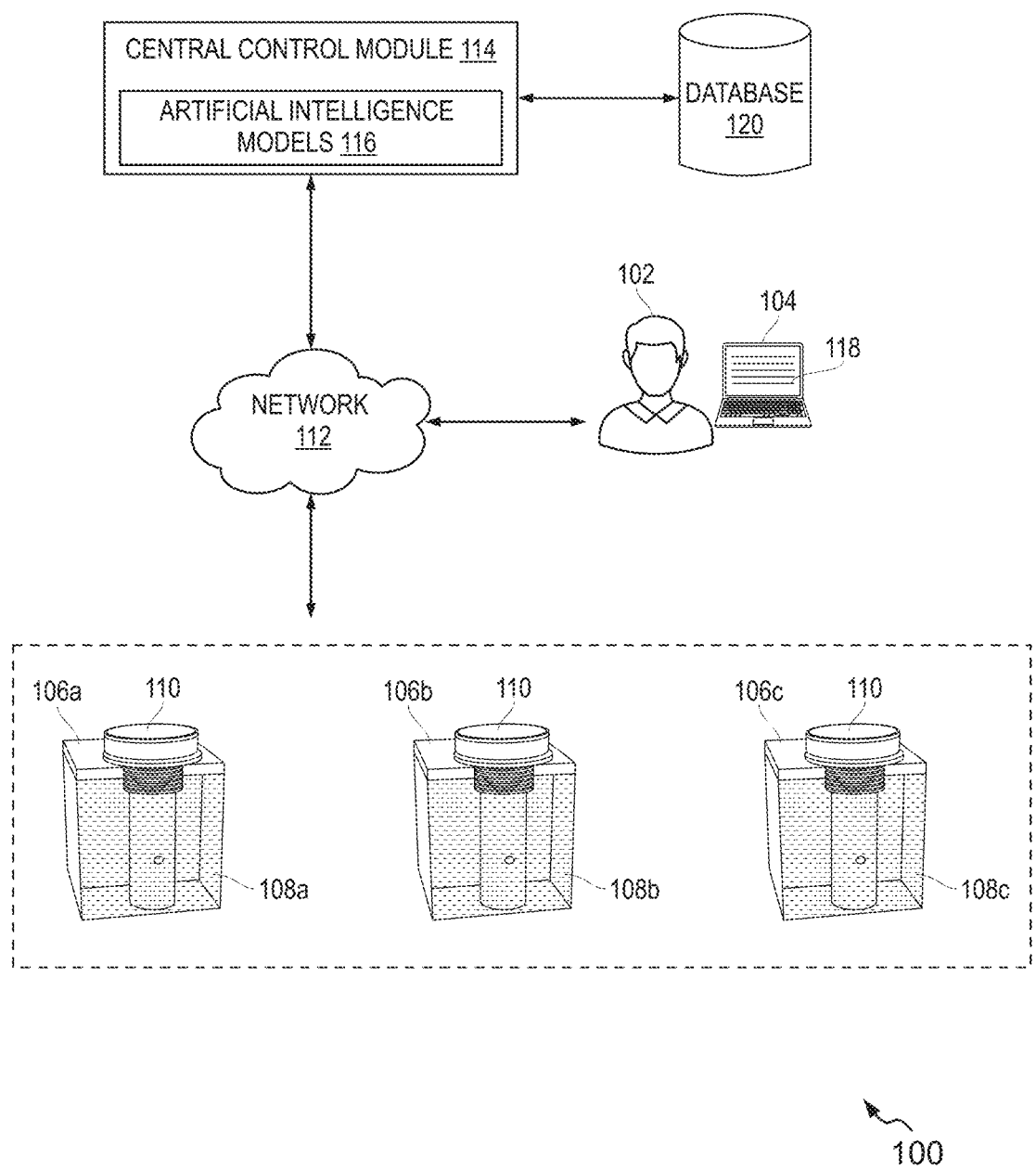
FIG. 1 illustrates an example representation of an environment related to at least some example embodiments of the present disclosure.

FIG. 1 illustrates an example representation of an environment 100 related to at least some example embodiments of the present disclosure. Although the environment 100 is presented in one arrangement, other arrangements are also possible where the parts of the environment 100 (or other parts) are arranged or interconnected differently. The environment 100 corresponds to a system for determining fluid quality. In one example, the system disclosed in the environment 100 may be configured to determine the quality of a fluid such as, but not limited to, wine, bourbon, and the like. The present disclosure is described with reference to determining the fluid quality of the fluid, for example, wine and/or bourbon. Alternatively, the system as disclosed in the environment 100 may be implemented to determine the fluid quality of other fluids such as alcoholic or non-alcoholic beverages.

The environment 100 includes a user 102 associated with a user device 104. The user device 104 may include at least a laptop computer, a phablet computer, a handheld personal computer, a Virtual Reality (VR) device, a netbook, a Web book, a tablet computing device, a smartphone, or other mobile computing devices. Further, the environment 100 includes a plurality of receptacles such as a receptacle 106a, a receptacle 106b, and a receptacle 106c. Each of the receptacles 106a, 106b, and 106c may be configured to store fluid such as fluid 108a, fluid 108b, and fluid 108c, respectively. The fluids 108a-108c may be one of wine and bourbon as explained above. For example, the fluid 108a stored in the receptacle 106a maybe wine, and the fluid 108b stored in the receptacle 106b may be bourbon. Further, each of the receptacles 106a-106c is equipped with a sensing device 110. Typically, the sensing device 110 is inserted into the receptacles 106a-106c storing the corresponding fluids 108a-108c via an aperture (not shown in FIG. 1) defined in the receptacles 106a-106c. The sensing device 110 is configured to determine one or more parameters related to the fluids 108a-108c stored in the corresponding receptacles 106a-106c, and ambient parameters of each of the receptacles 106a-106c which will be explained further in detail.

Various entities in the environment 100 may connect to a network 112 in accordance with various wired and wireless communication protocols, such as Transmission Control Protocol and Internet Protocol (TCP/IP), User Datagram Protocol (UDP), 2nd Generation (2G), 3rd Generation (3G), 4th Generation (4G), 5th Generation (5G) communication protocols, Long Term Evolution (LTE) communication protocols, Long Range (LoRa) Gateway Protocol or any combination thereof. In some instances, the network 112 may include a secure protocol (e.g., Hypertext Transfer Protocol (HTTP)), and/or any other protocol, or set of protocols. In an example embodiment, the network 112 may include, without limitation, a local area network (LAN), a wide area network (WAN) (e.g., the Internet), a mobile network, a virtual network, and/or another suitable public and/or private network capable of supporting communication among two or more of the entities illustrated in FIG. 1, or any combination thereof.

The environment 100 further includes a central control module 114. In an embodiment, the central control module 114 may be embodied in at least one computing device in communication with the network 112. In an embodiment, the central control module 114 may be embodied in the user device 104. In another embodiment, the central control module 114 may be an individual entity located remotely and communicably coupled to the entities of FIG. 1 via the network 112. The central control module 114 may be specifically configured, via executable instructions to perform one or more of the operations described herein. In general, the central control module 114 is configured to predict the fluid quality of the fluid (e.g., the fluid 108a) stored in the receptacle (e.g., the receptacle 106a) which will be explained further in detail. Further, the central control module 114 may be configured to host and manage an application 118. The application 118 is a set of computer-executable codes configured to allow the user 102 to track and/or visualize the fluid quality of the fluids 108a-108c stored in the corresponding receptacles 106a-106c. In one embodiment, the application 118 may be accessed as a web-based application on the user device 104. In another embodiment, the user device 104 may access an instance of the application 118 from the central control module 114 for installation on the user device 104 using application stores associated with operating systems such as Apple IOS®, Android™ OS, Google Chrome OS, Symbian OS®, Windows Mobile® OS, and the like.

In an embodiment, the user 102 may be an individual associated with managing the fluid quality of the fluids 108a-108c in the corresponding receptacles 106a-106c. In another embodiment, the user 102 may be a worker or a technician in a winery production industry and is associated with tracking and monitoring the fluid quality of the fluids 108a-108c in the corresponding receptacles 106a-106c. Herein, the fluid quality may correspond to determining the aging of the fluid (e.g., wine or bourbon) stored in the receptacles i.e., the receptacles 106a-106c.

In particular, the sensing device 110 inserted in the receptacle 106a is configured to determine the one or more parameters associated with the fluid 108a and the ambient parameters of the receptacle 106a. The sensing device 110 may include a plurality of sensors configured to detect the parameters related to the fluid 108a and the ambient parameters of the receptacle 106a. The parameters related to the fluid 108a (e.g., wine) may include but are not limited to, acidic concentration/acidity, pH value, alcohol content, sugar content, phenolic compounds, volatile compounds, fluid level measurement, color, turbidity, and fluid temperature. The ambient parameters of the receptacle 106a may include but are not limited to, ambient temperature and humidity. The sensing device 110 transmits the parameters of the fluid 108a and the ambient parameters of the receptacle 106a to the central control module 114 for determining the fluid quality of the fluid 108a via a communication interface (not shown in FIG. 1) associated with the sensing device 110. For example, the sensing device 110 may communicate with the central control module 114 using wireless communication protocols. Some examples of the wireless communication protocols may include, but are not limited to, Near-Field Communication (NFC), Wireless Fidelity (Wi-Fi), Bluetooth, and the like.

Thereafter, the central control module 114 implements one or more Artificial Intelligence (AI) models 116 to predict the fluid quality of the fluid 108a stored in the receptacle 106a. Specifically, the AI models 116 may access predefined fluid quality profiles stored in a database 120 associated with the central control module 114 to predict the fluid quality of the fluid 108a stored in the receptacle 106a which will be explained further in greater detail. Further, the central control module 114 may render the fluid quality of the fluid 108a in the receptacle 106a on the user device 104. As such, the user 102 may access the real-time fluid quality of the fluid 108a in the receptacle 106a by providing inputs in the application 118 equipped in the user device 104. Thus, this approach provides real-time testing of the fluid 108a without manual intervention, enables continuous monitoring of the fluid 108a in the receptacle 106a, provides immediate insights into the fluid 108a to monitor threats throughout the life cycle, and results in improved wine quality tracking. Similarly, one or more operations performed for determining the fluid quality of the fluid 108a stored in the receptacle 106a may be implemented to the fluids 108b and 108c stored in the corresponding receptacles 106b and 106c, therefore they are not reiterated herein for the sake of brevity.

The number and arrangement of systems, devices, and/or networks shown in FIG. 1 are provided as an example. There may be other systems, devices, and/or networks; fewer systems, devices, and/or networks; different systems, devices, and/or networks, and/or differently arranged systems, devices, and/or networks than those shown in FIG. 1. Furthermore, two or more systems or devices shown in FIG. 1 may be implemented within a single system or device, or a single system or device shown in FIG. 1 may be implemented as multiple, distributed systems or devices.

Figure 2A:
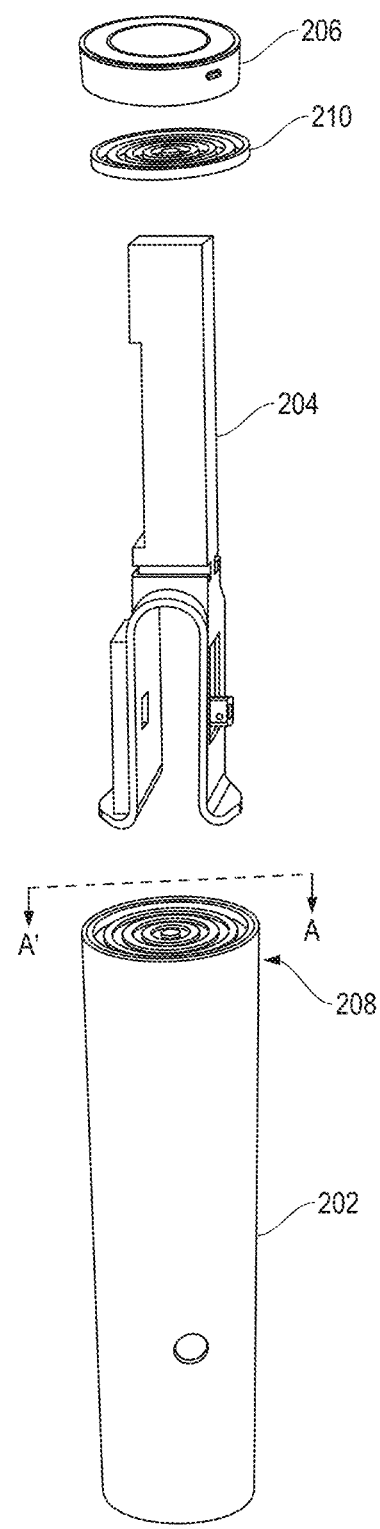
FIG. 2A illustrates an exploded view of a sensing device, in accordance with an embodiment of the present disclosure.

FIG. 2A illustrates an exploded view of the sensing device 110, in accordance with an embodiment of the present disclosure. The sensing device 110 includes an outer housing 202. The outer housing 202 is configured to be an elongated structure or a cylindrical structure. Alternatively, the outer housing 202 may be configured in various structural configurations as per the design feasibility and requirements. The outer housing 202 may be made of food-grade materials, for example, steel, aluminum, or any other materials as per the design feasibility and requirements. In an embodiment, the outer housing 202 may be a unitary structure. In another embodiment, the outer housing 202 may include two semi-circular structure that are detachably coupled to each other to form the outer housing 202. It is to be noted that the components (e.g., the outer housing 202) of the sensing device 110 that are in contact with the fluid 108*a* should be made of materials that are unreactive or non-responsive to the fluid 108*a*. As a result, the fluid quality of the fluid 108*a* is predicted accurately.

Further, the sensing device 110 includes an inner housing 204. The inner housing 204 may be configured to be inserted within the outer housing 202. The inner housing 204 may be configured to support at least one or more components and electronic circuitry of the sensing device 110 which will be explained further in detail. Furthermore, the sensing device 110 includes an enclosure 206. The enclosure 206 includes a second coupling member (see, 404 of FIG. 4) on a bottom surface (see, 406 of FIG. 4) of the enclosure 206. The enclosure 206 may be removably secured to a top portion 208 of the outer housing 202.

Figure 2B:
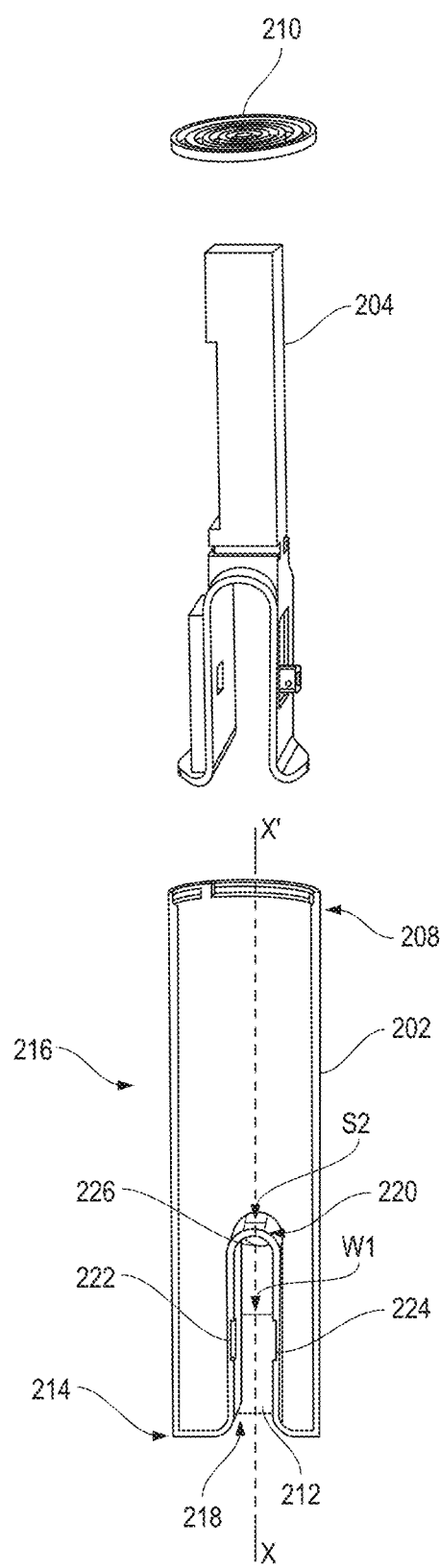
FIG. 2B illustrates an exploded view of the sensing device depicting an inner housing, a cross-section of an outer housing along a cross-sectional axis A-A', and a first coupling member of the sensing device, in accordance with an embodiment of the present disclosure.
Figure 2C:
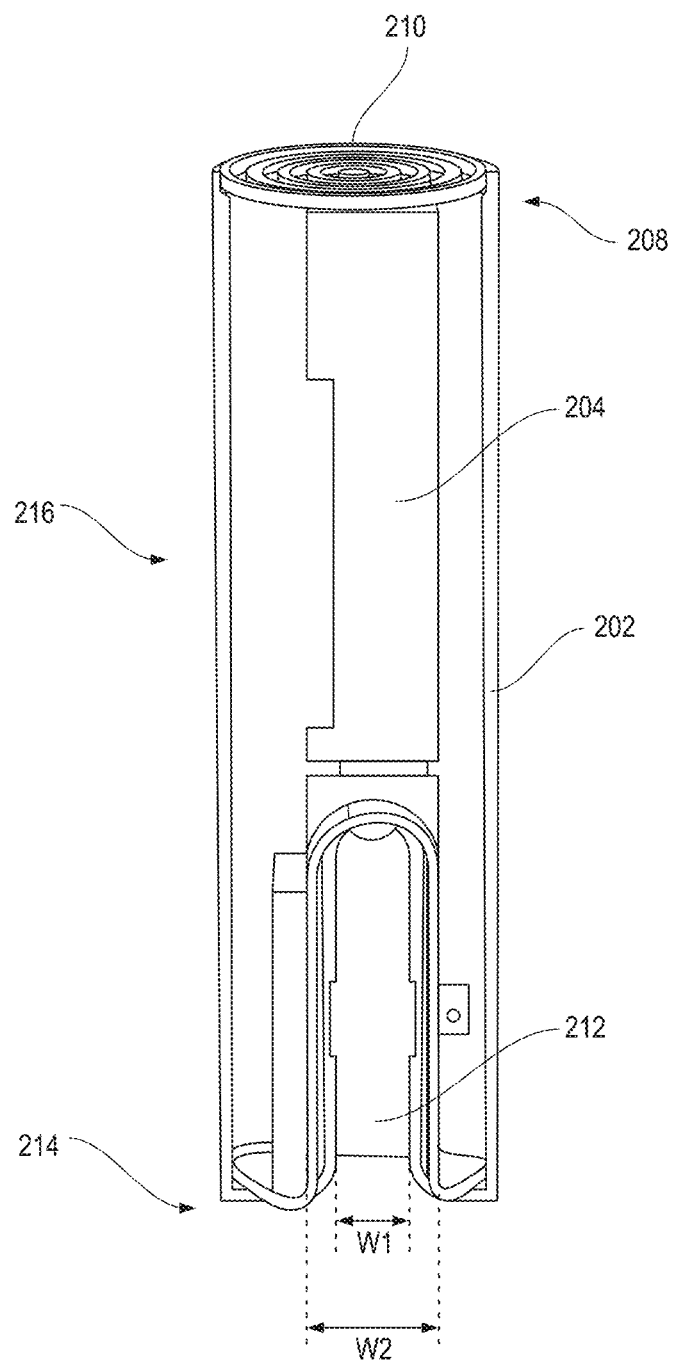
FIG. 2C illustrates a schematic representation of securing the inner housing to the outer housing, in accordance with an embodiment of the present disclosure.

FIG. 2B illustrates an exploded view of the sensing device 110 depicting the inner housing 204, a cross-section of the outer housing 202 along a cross-sectional axis A-A', and a first coupling member 210 of the sensing device 110, in accordance with an embodiment of the present disclosure. As shown, the outer housing 202 includes a cavity 212 extending from a bottom portion 214 to a central portion 216 of the outer housing 202 along a longitudinal axis X-X' of the outer housing 202. The cavity 212 includes open configuration 218 at the bottom portion 214 for receiving a portion of the fluid (e.g., the fluid 108*a*) stored in the receptacle (e.g., the receptacle 106*a*) while the sensing device 110 is inserted into the receptacle 106*a*. Further, the cavity 212 includes a closed configuration 220 proximate to the central portion 216 of the outer housing 202. In other words, the cavity 212 configured in the outer housing 202 conforms to an inverted U-shaped structure. The outer housing 202 includes at least one air vent 226 configured proximate to the closed configuration 220 of the cavity 212. The at least one air vent 226 is adapted to allow the outflow of air while the portion of the fluid 108*a* enters the cavity 212. In other words, the air vents 226 allow the air to flow outside of the cavity 212 for allowing the portion of the fluid 108*a* to enter the cavity 212. In an embodiment, two air vents (such as the air vents 226) are configured on diametrically opposite sides of the outer housing 202. Further, the first coupling member 210 is mounted to the top portion 208 of the enclosure 206 (as shown in FIG. 2C).

Figure 3:
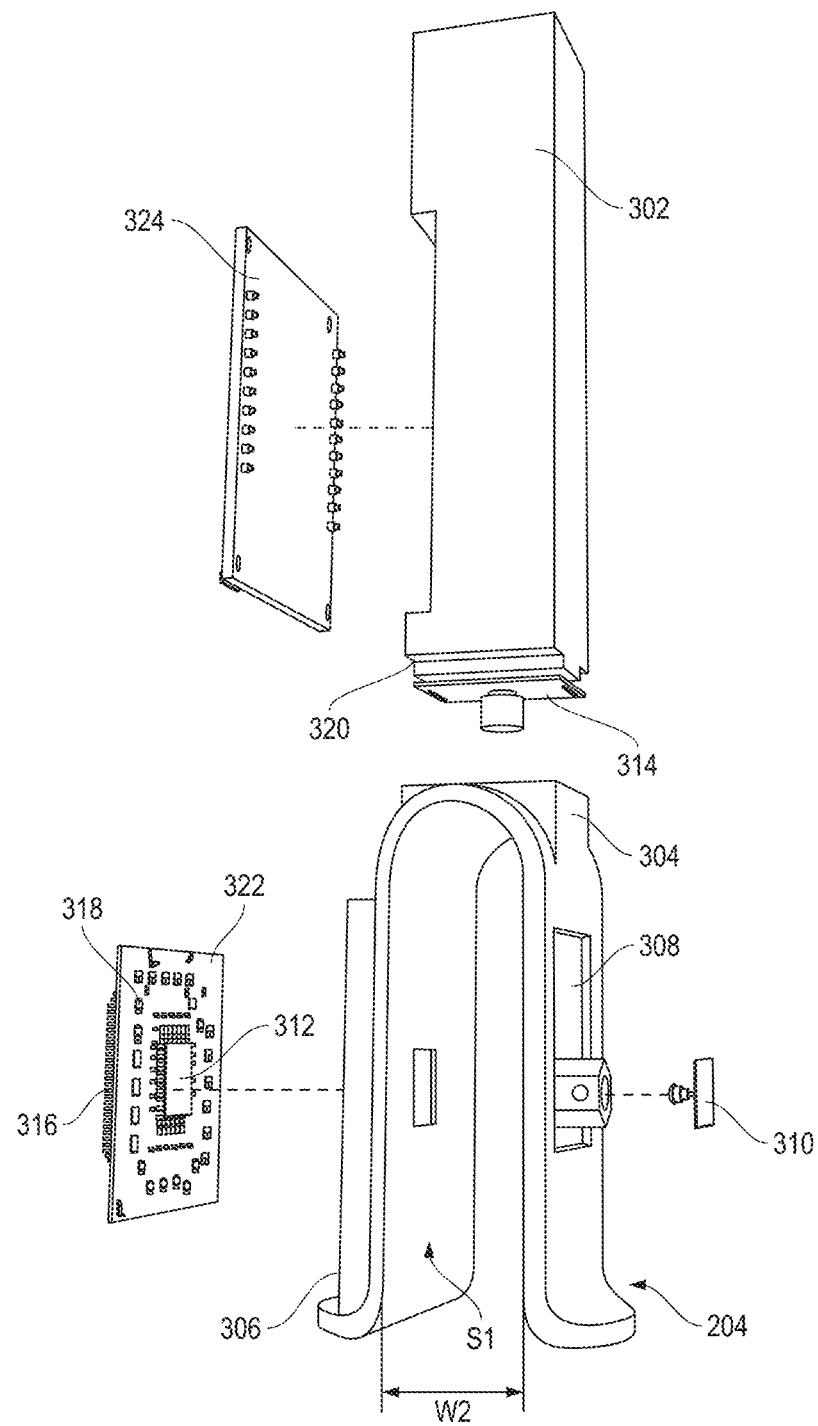
FIG. 3 illustrates an exploded view of the inner housing, in accordance with an embodiment of the present disclosure.

Referring to FIG. 3 in conjunction with FIG. 2B, the inner housing 204 includes a top part 302 and a bottom part 304. The top part 302 and the bottom part 304 are detachably coupled to each other to form the inner housing 204. Alternatively, the inner housing 204 including the top part 302 and the bottom part 304 may be configured to a unitary structure. Similar to the outer housing 202, the inner housing 204 may be made using food-grade materials, for example, steel, aluminum, or any other materials as per the design feasibility and requirements.

The sensing device 110 further includes a control circuitry 324. The control circuitry 324 may be mounted to the top part 302 of the inner housing 204. In an embodiment, the control circuitry 324 may be located remotely and may be communicably coupled to a plurality of sensors of the sensing device 110. The control circuitry 324 includes suitable logic and/or circuitry for performing one or more operations described herein. Typically, the control circuitry 324 may be configured to control operating conditions, data transmission, etc., associated with the sensing device 110 which will be explained further in detail.

Further, the bottom part 304 is configured in conformity with the cavity 212 of the outer housing 202. In other words, the bottom part 304 of the inner housing 204 is configured to be the inverted U-shaped structure similar to the cavity 212. This allows the bottom part 304 to snuggly fit onto the cavity 212 of the outer housing 202 while the inner housing 204 is inserted within the outer housing 202 through the top portion 208 of the outer housing 202. It is to be noted that a width dimension 'W1' of the inverted U-shaped structure of the bottom part 304 is slightly greater than a width dimension 'W2' of the inverted U-shaped structure of the cavity 212. The width dimensions 'W1' and 'W2' are defined such that an inner circumferential surface 'S1' of the bottom part 304 of the inner housing 204 abuts an outer circumferential surface 'S2' of the cavity 212 while the bottom part 304 of the inner housing 204 is inserted into the outer housing 202 (as shown in FIG. 2C).

Furthermore, the bottom part 304 of the inner housing 204 is configured with a first chamber 306 and a second chamber 308. As shown, the first chamber 306 and the second chamber 308 are configured on opposite sides of the bottom part 304. Alternatively, the first chamber 306 and the second chamber 308 may be configured at any other location of the inner housing 204 as per the design feasibility and requirements.

The sensing device 110 may include a radiating light source 310. The radiating light source 310 may be disposed in a second chamber 308 configured in the bottom part 304. As shown in FIG. 2C, the second chamber 308 is positioned in parallel to a second window (see, 224 of FIG. 2B) defined in the cavity 212 while the inner housing 204 is secured in the outer housing 202. The radiating light source 310 is communicably coupled to the control circuitry 324. The control circuitry 324 may operate the radiating light source 310 to emit radiating light onto the portion of the fluid 108*a* stored in the cavity 212 through the second window 224 of the cavity 212. The radiating light source 310 may include Light Emitting Diodes (LEDs) configured to emit the radiating light of different wavelengths between the visible light region to the infrared region. Alternatively, the radiating light source 310 may include, but not limited to, Tungsten-Halogen Lamps, Laser Diodes, and the like. The radiating light emitted by the radiating light source 310 is directed toward the portion of the fluid 108*a* in the cavity 212 through the second window 224. The radiating light penetrates through the fluid 108*a* and interacts with the molecules of the fluid 108*a*. Typically, specific wavelengths of the radiating light emitted by the radiating light source 310 are absorbed by different molecular bonds (such as O—H, C—H, and N—H bonds) of the fluid 108*a* (e.g., wine) stored in the cavity 212.

Furthermore, the bottom part 304 of the inner housing 204 is configured to accommodate the plurality of sensors. The plurality of sensors may include at least a first sensor unit 312, a second sensor unit 314, a third sensor unit 316, a fourth sensor unit 318, and a fifth sensor unit (see, 402 of FIG. 4).

The first sensor unit 312 and the third sensor unit 316 may be disposed in the first chamber 306 configured in the bottom part 304 of the inner housing 204. As shown in FIG. 2C, the first chamber 306 is positioned in parallel to a first window (see, 222 of FIG. 2B) of the cavity 212 while the inner housing 204 is secured in the outer housing 202. The first sensor unit 312 and the third sensor unit 316 may be mounted onto a Printed Circuit Board (PCB) 322. The PCB 322 including the first sensor unit 312 and the third sensor unit 316 is disposed in the first chamber 306. In this way, the first sensor unit 312 and the third sensor unit 316 may be configured to monitor the one or more parameters of the portion of the fluid 108a in the cavity 212 through the first window 222 of the cavity 212 which will be explained further in detail.

The first sensor unit 312 is configured to detect at least acidic concentration, alcohol content, sugar content (i.e., sugars and residual sugars), pH value, phenolic compounds, and volatile compounds related to the fluid 108a stored in the receptacle 106a. The first sensor unit 312 detects the aforementioned parameters of the fluid 108a based at least on processing the radiating light received at the first sensor unit 312 upon interaction with the portion of the fluid 108a in the cavity 212. For example, the first sensor unit 312 may be an Infrared (IR) sensor or a Near Infrared (NIR) sensor. In this scenario, the radiating light source 310 may be operated to emit radiating light of wavelength between 700 nanometers (nm) to 2500 nm). The radiating light upon interaction with the fluid 108a is received at the first sensor unit 312, The first sensor unit 312 may measure the absorption intensity of the radiating light by molecular bonds, particularly C—H, O—H, and N—H bonds of the fluid 108a in the cavity 212. The first sensor unit 312 may generate an absorption spectrum, which is a plot of absorbance (or transmittance) versus wavelength for each of the parameters (such as the acidic concentration, the alcohol content, pH value, phenolic compounds, and volatile compounds) associated with the fluid 108a. The acidic concentration of the fluid 108a may include detecting the level of acetic acid, malic acid, lactic acid, and titratable acid of the fluid 108a. Further, the volatile compounds may include Sulfur dioxide ($SO_2$).

The third sensor unit 316 may be configured to determine the color and turbidity of the one or more parameters related to the fluid 108a. The third sensor unit 316 determines the color and turbidity of the fluid 108a based at least on processing the radiating light received at the third sensor unit 316 upon interaction with the portion of the fluid 108a in the cavity 212. For example, the third sensor unit 316 may be a visible light sensor. In this scenario, the radiating light source 310 may be operated to emit the radiating light of wavelength between 380 nm to 750 nm. The radiating light upon interacting with the fluid 108a in the cavity 212 is received at the third sensor unit 316 through the first window 222. The third sensor unit 316 measures the absorption, reflection, and transmission of the radiating light by the portion of the fluid 108a in the cavity 212 to determine the color and clarity of the wine (i.e., the fluid 108a). It is to be noted that the first window 222 and the second window 224 may be provided with a cover member (not shown in FIGS.) made of transparent or translucent materials for enabling transmission of the radiating therethrough.

Further, the second sensor unit 314 is disposed in the inner housing 204. Typically, the second sensor unit 314 is mounted to a bottom side 320 of the top part 302 and positioned at the closed configuration 220 of the cavity 212. For example, the second sensor unit 314 is an ultrasonic sensor. The second sensor unit 314 may emit ultrasonic waves and measure the time it takes for the waves to reflect from the surface of the fluid 108a. Further, the second sensor unit 314 computes the distance based on the time delay between the emitted and received waves to determine the fluid level measurement.

The fourth sensor unit 318 is disposed in the bottom part 304 of the inner housing 204. The fourth sensor unit 318 may be mounted to the PCB 322 that is disposed in the first chamber 306. The fourth sensor unit 318 is communicably coupled to the control circuitry 324. The fourth sensor unit 318 may include a temperature sensor. The fourth sensor unit 318 is configured to detect a fluid temperature of the fluid 108a stored in the receptacle 106a.

Figure 4:
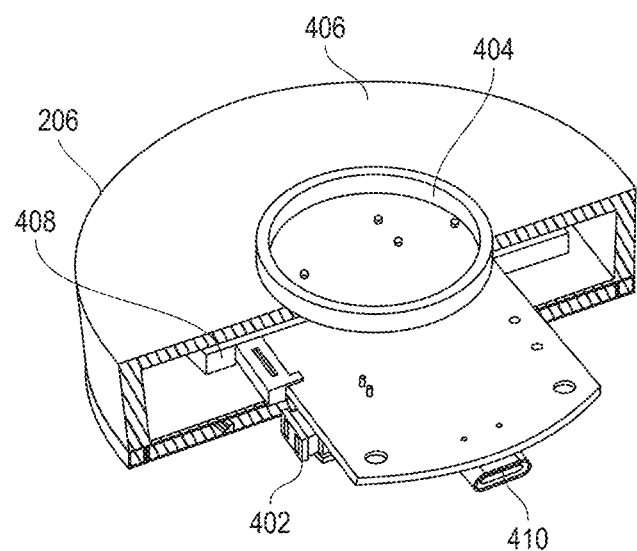
FIG. 4 illustrates a cross-sectional view of an enclosure of the sensing device, in accordance with an embodiment of the present disclosure.

Referring to FIG. 4 in conjunction with FIG. 2B, the fifth sensor unit 402 is disposed in the enclosure 206. The fifth sensor unit 402 is communicably coupled to the control circuitry 324. The fifth sensor unit 402 is configured to determine at least the ambient parameters of the receptacle 106a. The ambient parameters of the receptacle 106a may include, but not limited to, an ambient temperature and humidity. The enclosure 206 further includes the second coupling member 404. The second coupling member 404 is configured at the bottom surface 406 of the enclosure 206. The second coupling member 404 is configured to detachably couple with the first coupling member 210 while the enclosure 206 is removably secured to the top portion 208 of the outer housing 202. The first coupling member 210 and the second coupling member 404 may be made of magnetic materials. This allows a magnetic coupling of the first coupling member 210 and the second coupling member 404.

The sensing device 110 further includes a power source 408. The power source 408 is disposed in the enclosure 206. The power source 408 is operatively coupled to the second coupling member 404. Further, detachably coupling the first coupling member 210 and the second coupling member 404 enables power transmission from the power source 408 to at least the control circuitry 324 and the plurality of sensors (i.e., the first sensor unit 312, the second sensor unit 314, the third sensor unit 316, the fourth sensor unit 318, and the fifth sensor unit 402). The power source 408 may provide one of an alternating current output or a direct current output. In an embodiment, the power source 408 includes a direct current power source, such as a rechargeable battery (for example, a lithium-ion battery), operable to provide the required electrical power for the operation of the sensing device 110. Further, the power source 408 may include electrical and/or electronic components or circuits for enabling the use of wired or wireless charging. Alternatively, the power source 408 may include electrical and/or electronic components or circuits for enabling the use of alternating current to provide the required electrical power for the operation of the sensing device 110. Further, the sensing device 110 may include a charging port 410 to plug an electric line for receiving electric power for charging the power source 408.

Further, the sensing device 110 includes a fastening member. The fastening member may be configured proximate to the top portion 208 of the outer housing 202. The fastening member is snuggly secured to an aperture of the receptacle 106a while the outer housing 202 is being inserted into the receptacle 106a through the aperture. The structural configuration of the fastening member and its functionality is explained with reference to FIGS. 5A-5B, FIGS. 6A-6B, and FIG. 7.

Figure 5A:
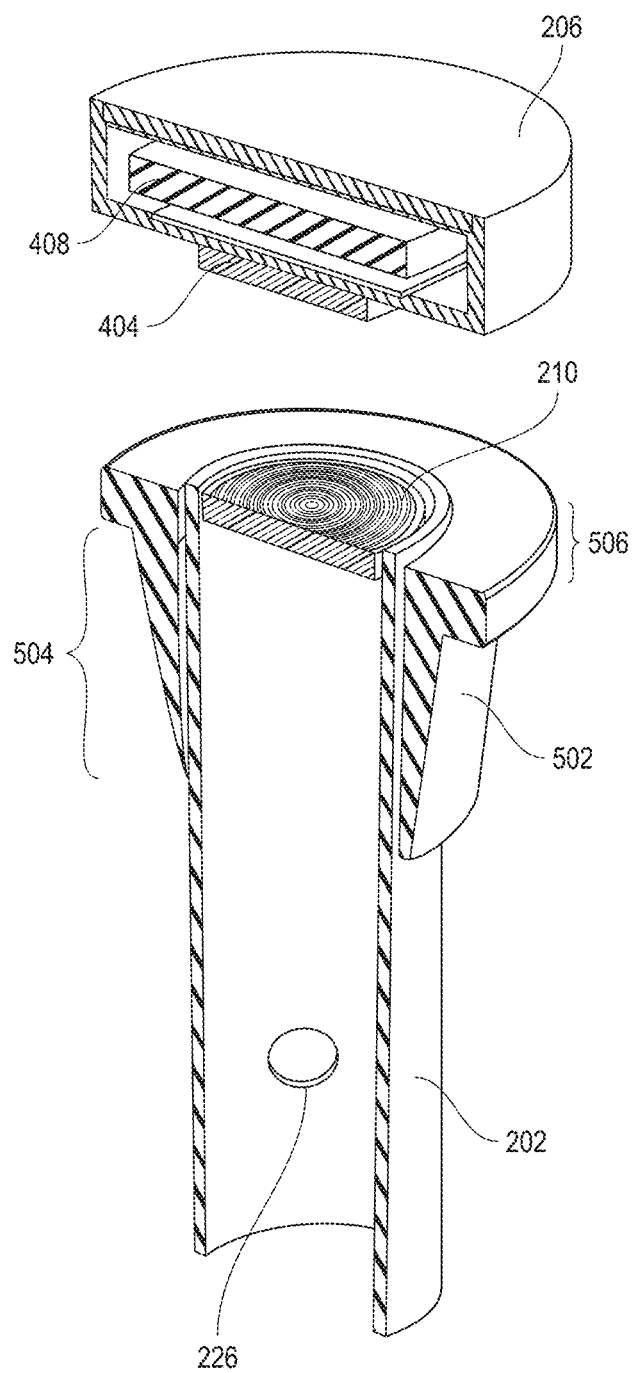
FIGS. 5A and 5B illustrate a schematic representation of the sensing device including a fastening member, in accordance with an embodiment of the present disclosure.
Figure 5B:
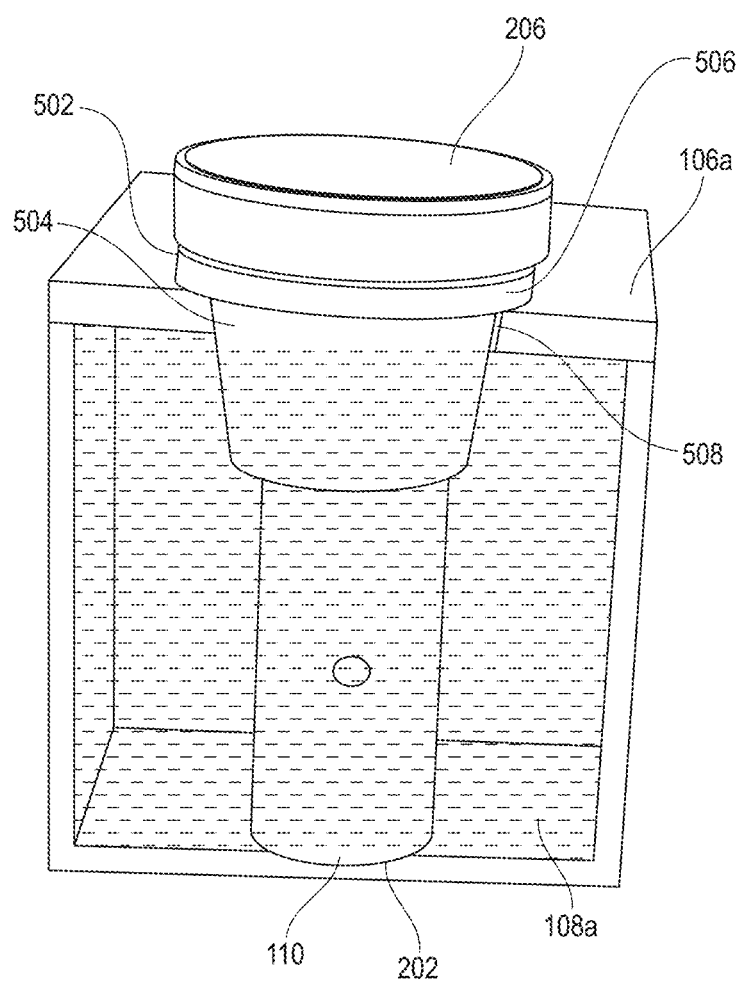
Figure 7:
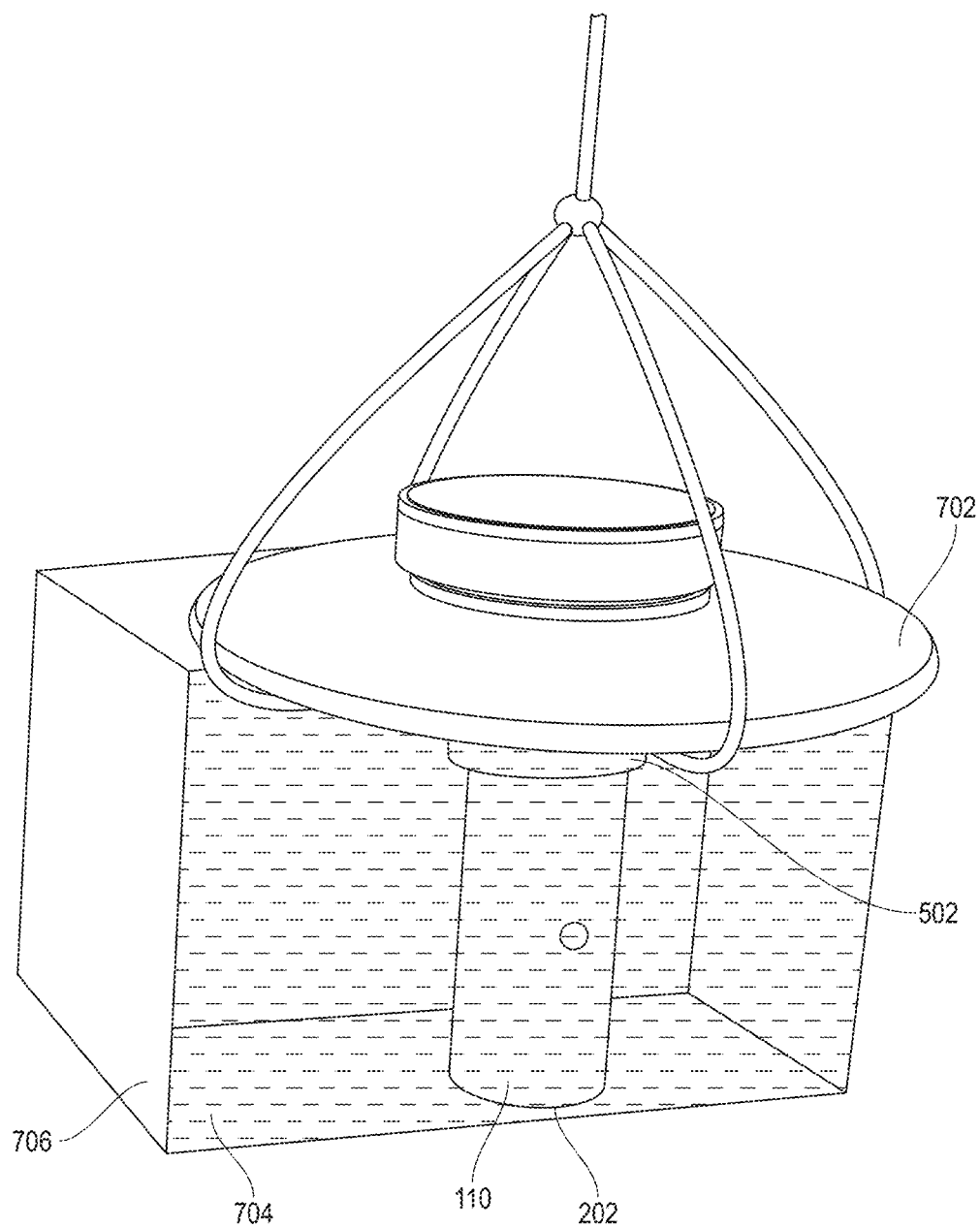
FIG. 7 illustrates a schematic representation of the sensing device including the fastening member of FIG. 5A mounted with a mounting structure, in accordance with another embodiment of the present disclosure.

Referring to FIG. 5A, the sensing device 110 includes a fastening member 502. In this scenario, the fastening member 502 may include a portion 504 configured with a tapered profile. The portion 504 (i.e., the tapered profile) of the fastening member 502 snuggly secures to an aperture (see, 508) while the outer housing 202 is inserted into the receptacle 106a through the aperture 508 (as shown in FIG. 5B). The fastening member 502 may be made of flexible materials such as silicone. The tapered profile (i.e., the portion 504) allows the insertion of the sensing device 110 to the receptacle configured with an aperture of various dimensions. In this scenario, as the sensing device 110 (or the outer housing 202) secured with the fastening member 502 is being inserted into the aperture 508, the fastening member 502 is snuggly secured to the aperture 508 to form an air-tight seal between the sensing device 110 and the aperture 508. In this way, the sensing device 110 is suspended in the receptacle 106a. It is to be noted that the enclosure 206 removably secured to the top portion 208 of the outer housing 202 and a portion 506 of the fastening member 502 are positioned outside the receptacle 106a while the sensing device 110 is secured to the receptacle 106a. In other words, the dimensions of the tapered profile (i.e., the portion 504) of the fastening member 502 configured in conformity with the dimensions of the aperture 508 enable the snug mount between the portion 504 of the fastening member 502 and the aperture 508. As a result, the enclosure 206 and the portion 506 of the fastening member 502 are positioned outside the receptacle 106a. The portion 506 of the fastening member 502 may be dimensioned greater than the dimensions of the tapered profile (i.e., the portion 504) and the aperture 508. As explained above, once the sensing device 110 is suspended in the receptacle 106a, the portion of the fluid 108a enters the cavity 212 (as shown in FIG. 7). Further, the sensing device 110 disposed in the receptacle 106a is configured to track the one or more parameters of the fluid 108a in the receptacle 106a as explained above.

Figure 6A:
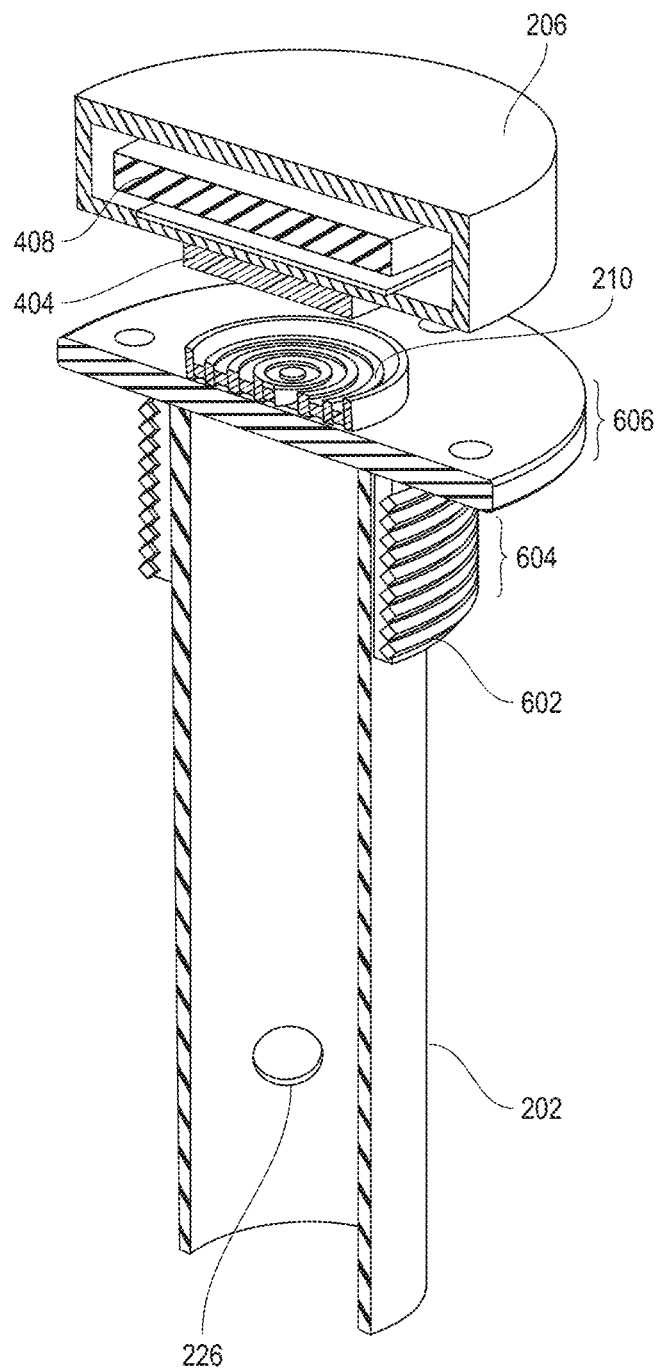
FIGS. 6A and 6B illustrate a schematic representation of the sensing device including a fastening member, in accordance with another embodiment of the present disclosure.
Figure 6B:
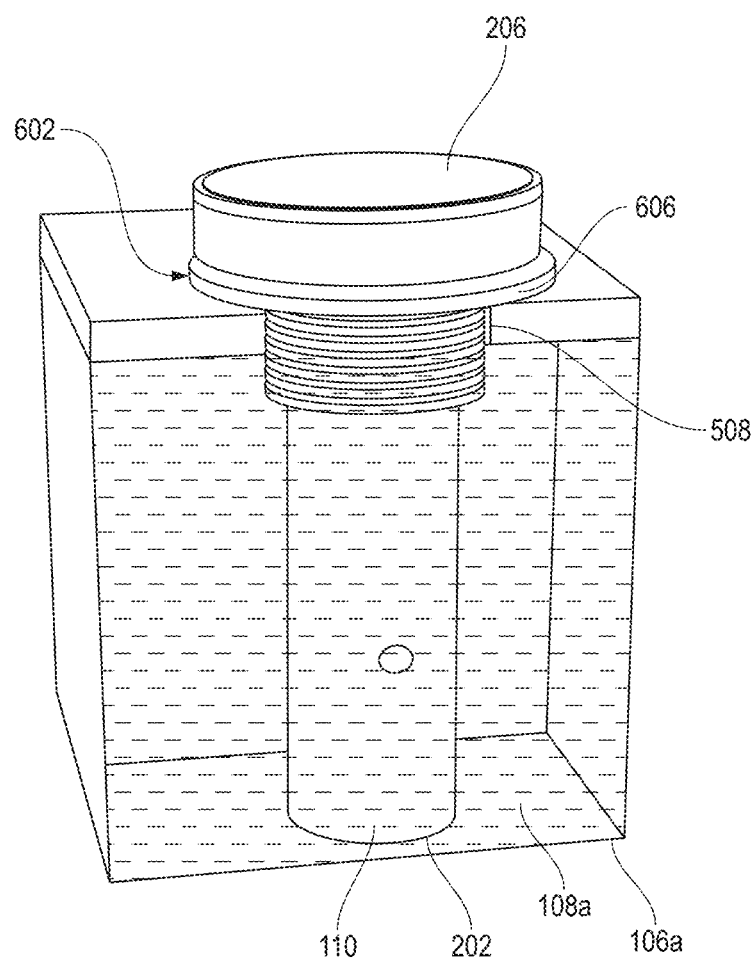

Referring to FIG. 6A, the sensing device 110 includes a fastening member 602. In this scenario, the fastening member 602 may include a plurality of engagement members 604 configured at the top portion 208 of the outer housing 202. The engagement members 604 of the fastening member 602 is configured to removably engage with an aperture (see, 508) while the outer housing 202 is inserted into the receptacle 106a through the aperture 508 (as shown in FIG. 6B). Specifically, the aperture 508 may be configured with a plurality of complementary engagement members (not shown in FIGS.). The engagement members 604 is configured to removably engage with the complementary engagement members of the aperture 508 for disposing the sensing device 110 within the receptacle 106a (as shown in FIG. 6B). It is to be noted that the enclosure 206 removably secured to the top portion 208 of the outer housing 202 and a portion 606 of the fastening member 602 are positioned outside the receptacle 106a while the sensing device 110 is secured to the receptacle 106a. The portion 606 of the fastening member 602 may be dimensioned greater than the dimensions of the plurality of engagement members 604 and the aperture 508.

Referring to FIG. 7, a mounting structure 702 may be secured over the fastening member 502 of the sensing device 110. In particular, the mounting structure 702 may be secured onto the tapered profile of the fastening member (as shown in FIG. 7). The mounting structure 702 may be used to suspend the sensing device 110 in a receptacle (such as a receptacle 706). In this scenario, the aperture of the receptacle 706 may be dimensioned greater than the dimensions of the fastening member 502, thus preventing the fastening member 502 from being secured to the aperture of the receptacle 706. The mounting structure 702 may be further secured with a securing means 708 secured to a fixed object (not shown in FIGS.). The securing means 708 holds the mounting structure 702 when secured to the fastening member 502 and the sensing device 110 when inserted into the receptacle 706. In particular, the mounting structure 702 is positioned on the surface of the receptacle 706 while the sensing device 110 is inserted into the receptacle 706. In this way, the sensing device 110 is suspended in the receptacle 706 for real-time tracking of the parameters of a fluid 704 (e.g., wine or bourbon) in the receptacle 706. In other words, the sensing device 110 is freely suspended in the receptacle 706 due to a combined operation of the mounting structure 702 supported on the receptacle 706, and the securing means 708 secured onto the mounting structure 702 and the fixed object.

Figure 8:
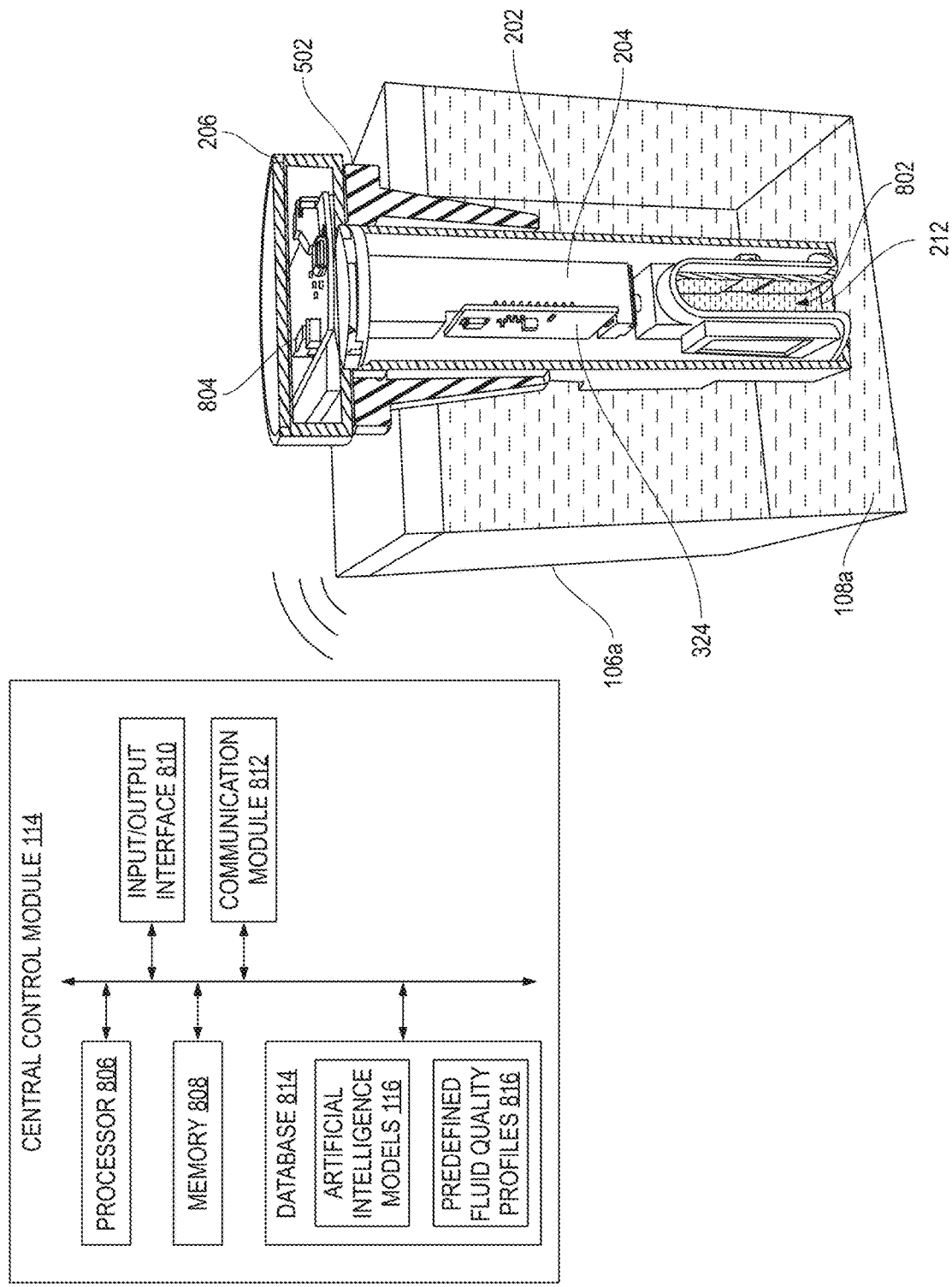
FIG. 8 illustrates a schematic representation of the sensing device inserted into a receptacle and a central control module, in accordance with an embodiment of the present disclosure.

FIG. 8 illustrates a schematic representation of the sensing device 110 inserted into the receptacle 106a and the central control module 114, in accordance with an embodiment of the present disclosure. As explained above, the sensing device 110 is inserted into the receptacle 106a for real-time tracking of the fluid 108a in the receptacle 106a. Further, a portion (see, 802) of the fluid 108a enters the cavity 212 as the outer housing 202 of the sensing device 110 is inserted into the receptacle 106a. The plurality of sensors (i.e., the first sensor unit 312, the second sensor unit 314, the third sensor unit 316, the fourth sensor unit 318, and the fifth sensor unit 402) determines the one or more parameters of the fluid 108a and the ambient parameters of the receptacle 106a. In one scenario, the parameters of the fluid 108a (e.g., wine or bourbon) may be acidic concentration/acidity, pH value, alcohol content, sugar content, phenolic compounds, volatile compounds, fluid level measurement, color, turbidity, and fluid temperature. The ambient parameters of the receptacle 106a may include, but not limited to, ambient temperature and humidity. Thereafter, the control circuitry 324 generates the sensory data based at least on processing the one or more parameters related to the fluid 108a stored in the receptacle 106a and the ambient parameters of the receptacle 106a. Further, the control circuitry 324 transmits the sensory data to the central control module 114 via a communication interface 804 housed in the enclosure 206.

The central control module 114 includes at least one processor, such as a processor 806 and a memory 808. It is noted that although the central control module 114 is depicted to include only one processor, the central control module 114 may include more processors therein. In an embodiment, the memory 808 is capable of storing machine-executable instructions. Further, the processor 806 is capable of executing the machine-executable instructions to perform one or more operations described herein. In an embodiment, the processor 806 may be embodied as a multi-core processor, a single-core processor, or a combination of one or more multi-core processors and one or more single-core processors. For example, the processor 806 may be embodied as one or more of various processing devices, such as a coprocessor, a microprocessor, a controller, a Digital Signal Processor (DSP), a processing circuitry with or without an accompanying DSP, or various other processing devices including integrated circuits such as, for example, an Application Specific Integrated Circuit (ASIC), a Field Programmable Gate Array (FPGA), a microcontroller unit (MCU), a hardware accelerator, a special-purpose computer chip, or the like. In an embodiment, the processor 806 may be configured to execute hard-coded functionality. In an embodiment, the processor 806 is embodied as an executor of software instructions, wherein the instructions may specifically configure the processor 806 to perform the algorithms and/or operations described herein when the instructions are executed.

The memory 808 may be embodied as one or more volatile memory devices, one or more non-volatile memory devices, and/or a combination of one or more volatile memory devices and non-volatile memory devices. For example, the memory 808 may be embodied as semiconductor memories (such as mask (ROM), programmable ROM (PROM, Erasable PROM (EPROM), flash memory, Random Access Memory (RAM), etc.), magnetic storage devices (such as hard disk drives, floppy disks, magnetic tapes, etc.), optical magnetic storage devices (e.g., magneto-optical disks), Compact Disc Read Only Memory (CD-ROM), Compact Disc Recordable (CD-R), Compact Disc Rewritable (CD-R/W), Digital Versatile Disc (DVD) and BLU-RAY® Disc (BD).

The central control module 114 further includes an Input/Output (I/O) module 810 (hereinafter referred to as an 'I/O module 810') and at least one communication module such as a communication module 812. In an embodiment, the I/O module 810 may include mechanisms configured to receive inputs (or sensory data from the plurality of sensors) and provide outputs to the user 102.

In an embodiment, the processor 806 may include I/O circuitry configured to control at least some functions of one or more elements of the I/O module 810, such as, for example, a speaker, a microphone, a display, and/or the like. The processor 806 and/or the I/O circuitry may be configured to control one or more functions of the one or more elements of the I/O module 810 through computer program instructions, for example, software and/or firmware, stored on a memory, for example, the memory 808, and/or the like, accessible to the processor 806.

The communication module 812 may include communication circuitry such as for example, a transceiver circuitry including antenna and other communication media interfaces to connect to a wired and/or wireless communication protocol. The communication circuitry may, in at least some example embodiments, enable the transmission of data signals and/or reception of signals from other network entities, such as the plurality of sensors, the user device 104, the control circuitry 324, or other entities of FIG. 1.

In an embodiment, the processor 806 receives the sensory data from the control circuitry 324 via a communication interface (such as the communication interface 804) associated with the sensing device 110. The processor 806 is configured to predict, by the one or more Artificial Intelligence (AI) models 116, the fluid quality of the fluid 108*a* stored in the receptacle 106*a* based at least on the sensory data. In particular, the fluid quality is determined by the AI models 116 by mapping the sensory data of the fluid 108*a* with a data model (i.e., a database 814) including a set of predefined fluid quality profiles 816.

It is understood that the AI models 116 are trained to predict the fluid quality of the fluid 108*a*. Typically, the central control module 114 may receive data samples related to the fluid quality of a set of fluid samples. In other words, a large group of fluid samples (ranging from old to fresh samples) of various wines or spirits (i.e., the fluid) are collected. Further, the processor 806 may determine a threshold range for each of the one or more parameters related to the set of fluid samples. The threshold range may include minimum and maximum values of each of the parameters. Further, the processor 806 may obtain reference values of the one or more parameters determined for the set of fluid samples. The reference values for each of the parameters for the set of fluid samples may be determined by an external computing device (e.g., an enzymatic analyzer). The processor 806 further generates the set of fluid quality profiles 816 based at least on the reference values and their corresponding threshold range determined for the one or more parameters associated with the set of fluid samples. The processor 806 creates the data model based at least on the set of fluid quality profiles 816 for training the AI models 116. The set of fluid quality profiles 816 corresponds to the predefined fluid quality profiles 816.

Similarly, the central control module 114 may be configured to receive the sensory data from the sensing device 110 equipped in the receptacles 106*b*-106*c*. The central control module 114 is configured to predict the fluid quality of the fluids 108*b*-108*c* in the receptacles 106*b*-106*c*. It is to be noted that the central control module 114 is capable of connecting to multiple sensing devices (such as the sensing device 110). Further, the processor 806 is configured to retrain the AI models 116 and update the set of predefined fluid profiles based on the real-time prediction of the fluid quality and the parameters of the fluid. The fluid quality of the fluids 108*a*-108*c* may be accessed through the application 118 equipped in the user device 104. In other words, the processor 806 may render the fluid quality of the fluids 108*a*-108*c* and the parameters of the fluids 108*a*-108*c* in the application 118 to provide access to the user 102.

Additionally, the processor 806 is configured to determine if the parameters and/or the fluid quality of the fluids 108*a*-108*c* is greater or less than the threshold range. In this scenario, the processor 806 is configured to transmit an alert notification to the user 102 in response to determining the parameters and/or the fluid quality of the fluids 108*a*-108*c* is greater or less than the threshold range. In one example, the alert notification may be transmitted to the user device 104 in the form of a text message. In another example, the alert notification may be rendered in the application 118.

Figure 9:
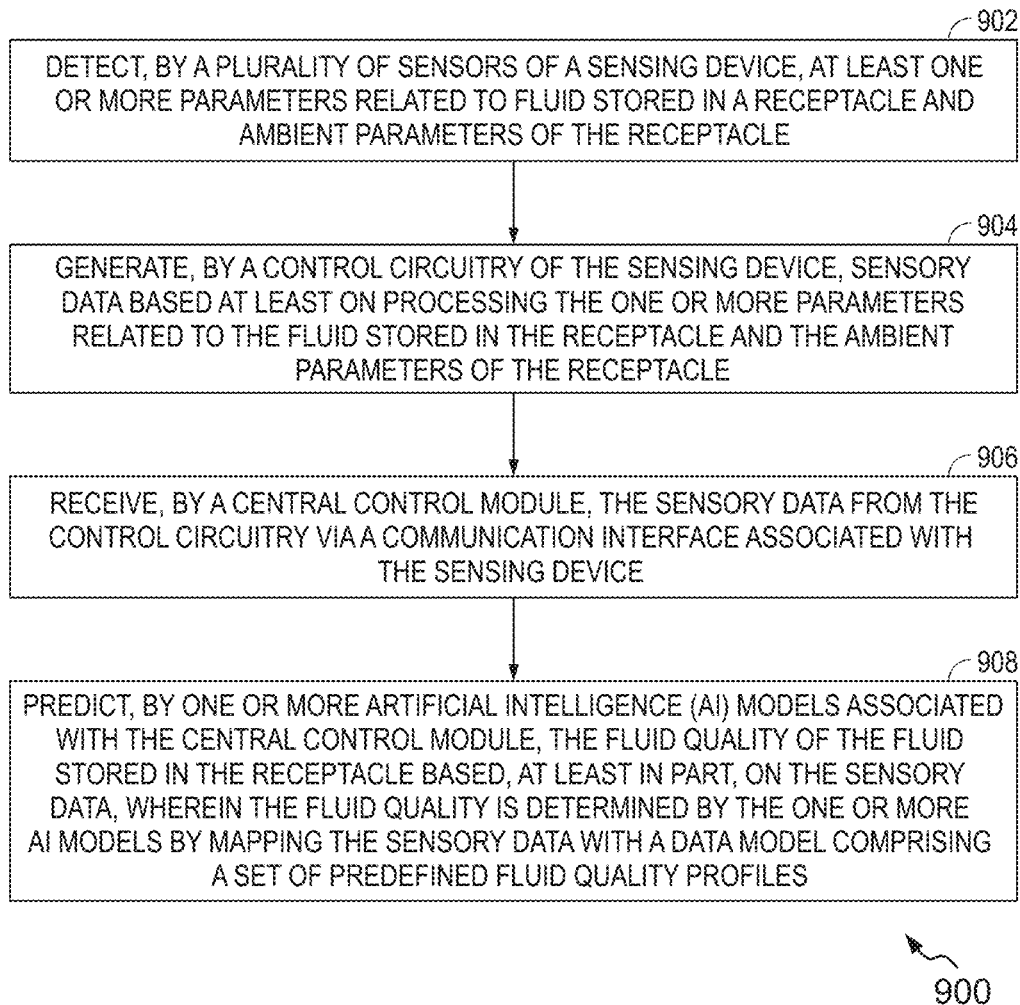
FIG. 9 illustrates a flow diagram of a method for determining quality of a fluid, in accordance with an embodiment of the present disclosure.

FIG. 9 illustrates a flow diagram of a method 900 for determining the fluid quality of the fluid, in accordance with an embodiment of the present disclosure. The method 900 depicted in the flow diagram may be executed by, for example, the sensing device 110 and the central control module 114. Operations of the flow diagram of the method 900, and combinations of the operations in the flow diagram of the method 900, maybe implemented by, for example, hardware, firmware, a processor, circuitry, and/or a different device associated with the execution of software that includes one or more computer program instructions. The method 900 starts at operation 902.

At operation 902, the method 900 includes detecting, by the plurality of sensors of the sensing device 110, at least one or more parameters related to fluid (e.g., the fluid 108*a*) stored in a receptacle (e.g., the receptacle 106*a*) and ambient parameters of the receptacle 106*a*.

At operation 904, the method 900 includes generating, by the control circuitry 324 of the sensing device 110, sensory data based at least on processing the one or more parameters related to the fluid 108*a* stored in the receptacle 106*a* and the ambient parameters of the receptacle 106*a*.

At operation 906, the method 900 includes receiving, by the central control module 114, the sensory data from the control circuitry 324 via a communication interface (such as the communication interface 804) associated with the sensing device 110.

At operation 908, the method 900 includes predicting, by the one or more artificial intelligence (AI) models 116 associated with the central control module 114, the fluid quality of the fluid 108*a* stored in the receptacle 106*a* based, at least in part, on the sensory data. The fluid quality is determined by the one or more AI models 116 by mapping the sensory data with a data model including the set of predefined fluid quality profiles 816. Further, the one or more operations for predicting the fluid quality are already explained with reference to FIGS. 1-8, therefore they are not reiterated herein for the sake of brevity.

Various embodiments of the disclosure, as discussed above, may be practiced with steps and/or operations in a different order, and/or with hardware elements in configurations, which are different than those which are disclosed. Therefore, although the disclosure has been described based on these exemplary embodiments, it is noted that certain modifications, variations, and alternative constructions may be apparent and well within the spirit and scope of the disclosure.

Although various exemplary embodiments of the disclosure are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A sensing device, comprising:
an outer housing comprising a cavity extending from a bottom portion to a central portion of the outer housing along a longitudinal axis of the outer housing, wherein the cavity is adapted to receive a portion of a fluid stored in a receptacle while the sensing device is inserted into the receptacle;
an inner housing comprising a top part and a bottom part, wherein the bottom part is configured in conformity with the cavity of the outer housing, for enabling the bottom part to snuggly fit onto the cavity of the outer housing while the inner housing is inserted within the outer housing through a top portion of the outer housing;
a plurality of sensors configured to detect at least one or more parameters related to the fluid stored in the receptacle and ambient parameters of the receptacle; and
a control circuitry communicably coupled to the plurality of sensors, the control circuitry configured to at least:
generate sensory data based at least on processing the one or more parameters related to the fluid stored in the receptacle and the ambient parameters of the receptacle, wherein the sensory data is transmitted to a central control module for determining fluid quality of the fluid stored in the receptacle.

2. The sensing device as claimed in claim 1, further comprising:
a radiating light source disposed in a second chamber configured in the bottom part, wherein the second chamber is positioned in parallel to a second window defined in the cavity while the inner housing is secured in the outer housing, the radiating light source configured to emit radiating light onto the portion of the fluid stored in the cavity through the second window of the cavity.

3. The sensing device as claimed in claim 1, further comprising:
a first sensor unit of the plurality of sensors housed in a first chamber configured in the bottom part of the inner housing, wherein the first chamber is positioned in parallel to a first window of the cavity while the inner housing is secured in the outer housing, the first sensor unit configured to at least detect acidic concentration, alcohol content, pH value, sugar content, phenolic compounds, and volatile compounds of the one or more parameters related to the fluid stored in the receptacle based at least on processing the radiating light received at the first sensor unit upon interaction with the portion of the fluid in the cavity;
a second sensor unit of the plurality of sensors disposed in the inner housing, the second sensor unit configured to determine at least fluid level measurement of the one or more parameters related to the fluid stored in the receptacle; and
a third sensor unit of the plurality of sensors disposed in the first chamber of the bottom part, the third sensor unit configured to at least determine color and turbidity of the one or more parameters related to the fluid based at least on processing the radiating light received at the third sensor unit upon interaction with the portion of the fluid in the cavity.

4. The sensing device as claimed in claim 1, further comprising:
a fourth sensor unit of the plurality of sensors disposed in the bottom part of the inner housing and communicably coupled to the control circuitry, wherein the fourth sensor unit is configured to detect a fluid temperature of the one or more parameters related to the fluid stored in the receptacle.

5. The sensing device as claimed in claim 1, further comprising:
a fifth sensor unit of the plurality of sensors communicably coupled to the control circuitry, the fifth sensor unit configured to determine at least the ambient parameters of the receptacle, the ambient parameters of the receptacle comprising at least an ambient temperature and humidity.

6. The sensing device as claimed in claim 1, further comprising:
a first coupling member secured to the top portion of the outer housing; and
an enclosure comprising a second coupling member configured on a bottom surface of the enclosure, wherein the second coupling member is adapted to be detachably coupled to the first coupling member while the enclosure is removably secured to the top portion of the outer housing.

7. The sensing device as claimed in claim 6, further comprising a power source disposed in the enclosure and operatively coupled to the second coupling member, wherein detachably coupling the first coupling member and the second coupling member enables power transmission from the power source to at least the control circuitry and the plurality of sensors.

8. The sensing device as claimed in claim 1, wherein the outer housing further comprises:
a fastening member configured proximate to the top portion of the outer housing, wherein the fastening member is snuggly secured to an aperture of the receptacle while the outer housing is being inserted into the receptacle through the aperture; and
at least one air vent configured on the outer housing and located proximate to a closed configuration of the cavity, the at least one air vent adapted to allow outflow of air while the portion of the fluid enters the cavity.

9. The sensing device as claimed in claim 8, wherein the fastening member comprises a portion configured with a tapered profile, wherein the portion of the tapered profile of the fastening member snuggly secures to the aperture while the outer housing is being inserted into the receptacle through the aperture.

10. The sensing device as claimed in claim 8, wherein the fastening member comprises a plurality of engagement members configured to removably engage with the aperture of the receptacle, thereby enabling the fastening member to be snuggly secured to the aperture.

11. A system for determining fluid quality, comprising:
a sensing device, comprising:
an outer housing comprising a cavity extending from a bottom portion to a central portion of the outer housing along a longitudinal axis of the outer housing, wherein the cavity is adapted to receive a portion of a fluid stored in a receptacle while the sensing device is inserted into the receptacle, an inner housing comprising a top part and a bottom part, wherein the bottom part is configured in conformity with the cavity of the outer housing, for enabling the bottom part to snuggly fit onto the cavity of the outer housing while the inner housing is inserted within the outer housing through a top portion of the outer housing, a plurality of sensors configured to detect at least one or more parameters related to the fluid stored in the receptacle and ambient parameters of the receptacle, and a control circuitry communicably coupled to the plurality of sensors, the control circuitry configured to generate sensory data based at least on processing the one or more parameters related to the fluid stored in the receptacle and the ambient parameters of the receptacle; and a central control module communicably coupled to the control circuitry, the central control module comprising a memory storing machine-executable instructions, and a processor communicably coupled to the memory, the processor configured to execute the machine-executable instructions to cause the central control module to at least:

receive the sensory data from the control circuitry via a communication interface associated with the sensing device, and predict, by one or more artificial intelligence (AI) models associated with the central control module, the fluid quality of the fluid stored in the receptacle based, at least in part, on the sensory data, wherein the fluid quality is determined by the one or more AI models by mapping the sensory data with a data model comprising a set of predefined fluid quality profiles.

12. The system as claimed in claim 11, further comprising:

a radiating light source disposed in a second chamber configured in the bottom part, wherein the second chamber is positioned in parallel to a second window defined in the cavity while the inner housing is secured in the outer housing, the radiating light source configured to emit radiating light onto the portion of the fluid stored in the cavity through the second window of the cavity;

a first sensor unit of the plurality of sensors housed in a first chamber configured in the bottom part of the inner housing, wherein the first chamber is positioned in parallel to a first window of the cavity while the inner housing is secured in the outer housing, the first sensor unit configured to at least detect at least acidic concentration, alcohol content, pH value, sugar content, phenolic compounds, and volatile compounds of the one or more parameters related to the fluid stored in the receptacle based at least on processing the radiating light received at the first sensor unit upon interaction with the portion of the fluid in the cavity;

a second sensor unit of the plurality of sensors disposed in the inner housing, the second sensor unit configured to determine at least fluid level measurement of the one or more parameters related to the fluid stored in the receptacle; and a third sensor unit of the plurality of sensors disposed in the first chamber of the bottom part, the third sensor unit configured to at least determine color and turbidity of the one or more parameters related to the fluid based at least on processing the radiating light received at the third sensor unit upon interaction with the portion of the fluid in the cavity.

13. The system as claimed in claim 11, further comprising:

a fourth sensor unit of the plurality of sensors disposed in the bottom part of the inner housing and communicably coupled to the control circuitry, wherein the fourth sensor unit is configured to detect a fluid temperature of the one or more parameters related to the fluid stored in the receptacle; and a fifth sensor unit of the plurality of sensors communicably coupled to the control circuitry, the fifth sensor unit configured to determine at least the ambient parameters of the receptacle, the ambient parameters of the receptacle comprising at least an ambient temperature and humidity.

14. The system as claimed in claim 11, wherein the central control module is further caused, at least in part, to:

train the one or more AI models to predict the fluid quality of the fluid stored in the receptacle, wherein training the one or more AI models comprises:

receive data samples related to the fluid quality of a set of fluid samples;

determine a threshold range for each of the one or more parameters related to the set of fluid samples;

obtain reference values of the one or more parameters determined for the set of fluid samples;

generate the set of fluid quality profiles based at least on the reference values and their corresponding threshold range determined for the one or more parameters associated with the set of fluid samples; and create the data model based at least on the set of fluid quality profiles for training the one or more AI models.

15. The system as claimed in claim 11, further comprising:

a first coupling member secured to the top portion of the outer housing;

an enclosure comprising a second coupling member configured on a bottom surface of the enclosure, wherein the second coupling member is adapted to be detachably coupled to the first coupling member while the enclosure is removably secured to the top portion of the outer housing; and a power source disposed in the enclosure and operatively coupled to the second coupling member, wherein detachably coupling the first coupling member and the second coupling member enables power transmission from the power source to at least the control circuitry and the plurality of sensors.

16. The system as claimed in claim 11, wherein the outer housing further comprises:

a fastening member configured proximate to the top portion of the outer housing, wherein the fastening member is snuggly secured to an aperture of the receptacle while the outer housing is being inserted into the receptacle through the aperture; and at least one air vent configured on the outer housing and located proximate to a closed configuration of the cavity, the at least one air vent adapted to allow outflow of air while the portion of the fluid enters the cavity.

17. The system as claimed in claim 16, wherein the fastening member comprises a portion configured with a tapered profile, wherein the portion of the tapered profile of the fastening member snuggly secures to the aperture while the outer housing is being inserted into the receptacle through the aperture.

18. The system as claimed in claim 16, wherein the fastening member comprises a plurality of engagement members configured to removably engage with the aperture of the receptacle, thereby enabling the fastening member to be snuggly secured to the aperture.

19. A method for determining fluid quality, comprising:
    detecting, by a plurality of sensors of a sensing device, at least one or more parameters related to fluid stored in a receptacle and ambient parameters of the receptacle;
    generating, by a control circuitry of the sensing device, sensory data based at least on processing the one or more parameters related to the fluid stored in the receptacle and the ambient parameters of the receptacle;
    receiving, by a central control module, the sensory data from the control circuitry via a communication interface associated with the sensing device; and
    predicting, by one or more artificial intelligence (AI) models associated with the central control module, the fluid quality of the fluid stored in the receptacle based, at least in part, on the sensory data, wherein the fluid quality is determined by the one or more AI models by mapping the sensory data with a data model comprising a set of predefined fluid quality profiles.

20. The method as claimed in claim 19, further comprising:
    training, by the central control module, the one or more AI models to predict the fluid quality of the fluid stored in the receptacle, wherein training the one or more AI models comprises:
    receiving data samples related to the fluid quality of a set of fluid samples;
    determining a threshold range for each of the one or more parameters related to the set of fluid samples;
    obtaining reference values of the one or more parameters determined for the set of fluid samples;
    generating the set of fluid quality profiles based at least on the reference values and their corresponding threshold range determined for the one or more parameters associated with the set of fluid samples; and
    creating the data model based at least on the set of fluid quality profiles for training the one or more AI models.

\* \* \* \* \*